United States Patent
Backus et al.

(10) Patent No.: US 10,136,991 B2
(45) Date of Patent: Nov. 27, 2018

(54) REPLACEMENT HEART VALVE IMPLANT

(71) Applicant: BOSTON SCIENTIFIC SCIMED INC., Maple Grove, MN (US)

(72) Inventors: Andrew J. H. Backus, San Francisco, CA (US); Ali Salahieh, Saratoga, CA (US); Cornelius M. Crowley, San Francisco, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 115 days.

(21) Appl. No.: 15/219,682

(22) Filed: Jul. 26, 2016

(65) Prior Publication Data

US 2017/0042672 A1 Feb. 16, 2017

Related U.S. Application Data

(60) Provisional application No. 62/204,073, filed on Aug. 12, 2015.

(51) Int. Cl.
*A61F 2/24* (2006.01)

(52) U.S. Cl.
CPC .......... *A61F 2/2418* (2013.01); *A61F 2/2409* (2013.01); *A61F 2220/0075* (2013.01);
(Continued)

(58) Field of Classification Search
CPC ...... A61F 2220/0075; A61F 2250/0069; A61F 2/2418; A61F 2/2439; A61F 2/24; A61F 2/2409
See application file for complete search history.

(56) References Cited

U.S. PATENT DOCUMENTS 2,682,057 A 6/1954 Lord
2,701,559 A 2/1955 Cooper
(Continued)

FOREIGN PATENT DOCUMENTS

CN 1338951 A 3/2002
DE 19532846 A1 3/1997
(Continued)

OTHER PUBLICATIONS

Andersen et al., "Transluminal implantation of artificial heart valves. Description of a new expandable aortic valve and initial results with implantation by catheter technique in closed chest pigs." Euro. Heart J., 13:704-708, May 1992.
(Continued)

*Primary Examiner* — Seema Mathew
(74) *Attorney, Agent, or Firm* — Seager, Tufte & Wickhem LLP

(57) ABSTRACT

A replacement heart valve implant may include a braided anchor member configured to actuate between a delivery configuration and a deployed configuration formed from a plurality of filaments, a circumferential seal member disposed about a distal portion of the anchor member and including a reinforcing band disposed at a distal end thereof, and a plurality of valve leaflets connected to the anchor member. The reinforcing band is secured to the anchor member adjacent a distal end of the anchor member by a plurality of lashings each attached to two individual filaments. The plurality of filaments defines a body section, a proximal crown section, and a distal crown section, wherein the proximal crown section includes a first plurality of end loops and a second plurality of end loops, wherein a proximalmost extent of the first plurality of end loops and the second plurality of end loops varies.

20 Claims, 6 Drawing Sheets

(52) U.S. Cl.
CPC . *A61F 2250/001* (2013.01); *A61F 2250/0007* (2013.01); *A61F 2250/0069* (2013.01)

(56) References Cited

U.S. PATENT DOCUMENTS

| | | | |
|---|---|---|---|
| 15,192 A | 6/1956 | Peale | |
| 2,832,078 A | 4/1958 | Williams | |
| 3,099,016 A | 7/1963 | Edwards | |
| 3,113,586 A | 12/1963 | Edmark, Jr. | |
| 3,130,418 A | 4/1964 | Head et al. | |
| 3,143,742 A | 8/1964 | Cromie | |
| 3,334,629 A | 5/1967 | Cohn | |
| 3,367,364 A | 2/1968 | Cruz, Jr. et al. | |
| 3,409,013 A | 11/1968 | Berry | |
| 3,445,916 A | 5/1969 | Schulte | |
| 3,540,431 A | 11/1970 | Mobin-Uddin | |
| 3,548,417 A | 12/1970 | Kischer et al. | |
| 3,570,014 A | 3/1971 | Hancock | |
| 3,587,115 A | 6/1971 | Shiley | |
| 3,592,184 A | 7/1971 | Watkins et al. | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Mouloupoulos | |
| 3,714,671 A | 2/1973 | Edwards et al. | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 3,997,923 A | 12/1976 | Possis | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,233,690 A | 11/1980 | Akins | |
| 4,265,694 A | 5/1981 | Boretos et al. | |
| 4,291,420 A | 9/1981 | Reul | |
| 4,297,749 A | 11/1981 | Davis et al. | |
| 4,323,358 A | 4/1982 | Lentz et al. | |
| 4,326,306 A | 4/1982 | Poler | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,423,809 A | 1/1984 | Mazzocco | |
| 4,425,908 A | 1/1984 | Simon | |
| 4,470,157 A | 9/1984 | Love | |
| 4,484,579 A | 11/1984 | Meno et al. | |
| 4,501,030 A | 2/1985 | Lane | |
| 4,531,943 A | 7/1985 | Van Tassel et al. | |
| 4,535,483 A | 8/1985 | Klawitter et al. | |
| 4,574,803 A | 3/1986 | Storz | |
| 4,580,568 A | 4/1986 | Gianturco | |
| 4,592,340 A | 6/1986 | Boyles | |
| 4,602,911 A | 7/1986 | Ahmadi et al. | |
| 4,605,407 A | 8/1986 | Black et al. | |
| 4,610,688 A | 9/1986 | Silvestrini et al. | |
| 4,612,011 A | 9/1986 | Kautzky | |
| 4,617,932 A | 10/1986 | Kornberg | |
| 4,643,732 A | 2/1987 | Pietsch et al. | |
| 4,647,283 A | 3/1987 | Carpentier et al. | |
| 4,648,881 A | 3/1987 | Carpentier et al. | |
| 4,655,218 A | 4/1987 | Kulik et al. | |
| 4,655,771 A | 4/1987 | Wallsten | |
| 4,662,885 A | 5/1987 | Dipisa, Jr. | |
| 4,665,906 A | 5/1987 | Jervis | |
| 4,680,031 A | 7/1987 | Alonso | |
| 4,692,164 A | 9/1987 | Dzemeshkevich et al. | |
| 4,705,516 A | 11/1987 | Barone et al. | |
| 4,710,192 A | 12/1987 | Liotta et al. | |
| 4,733,665 A | 3/1988 | Palmaz | |
| 4,755,181 A | 7/1988 | Igoe | |
| 4,759,758 A | 7/1988 | Gabbay | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,819,751 A | 4/1989 | Shimada et al. | |
| 4,829,990 A | 5/1989 | Thuroff et al. | |
| 4,834,755 A | 5/1989 | Silvestrini et al. | |
| 4,851,001 A | 7/1989 | Taheri | |
| 4,856,516 A | 8/1989 | Hillstead | |
| 4,865,600 A | 9/1989 | Carpentier et al. | |
| 4,872,874 A | 10/1989 | Taheri | |
| 4,873,978 A | 10/1989 | Ginsburg | |
| 4,878,495 A | 11/1989 | Grayzel | |
| 4,878,906 A | 11/1989 | Lindemann et al. | |
| 4,883,458 A | 11/1989 | Shiber | |
| 4,885,005 A | 12/1989 | Nashef et al. | |
| 4,909,252 A | 3/1990 | Goldberger | |
| 4,917,102 A | 4/1990 | Miller et al. | |
| 4,922,905 A | 5/1990 | Strecker | |
| 4,927,426 A | 5/1990 | Dretler | |
| 4,954,126 A | 9/1990 | Wallsten | |
| 4,966,604 A | 10/1990 | Reiss | |
| 4,969,890 A | 11/1990 | Sugita et al. | |
| 4,979,939 A | 12/1990 | Shiber | |
| 4,986,830 A | 1/1991 | Owens et al. | |
| 4,994,077 A | 2/1991 | Dobben | |
| 5,002,556 A | 3/1991 | Ishida et al. | |
| 5,002,559 A | 3/1991 | Tower | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,064,435 A | 11/1991 | Porter | |
| 5,080,668 A | 1/1992 | Bolz et al. | |
| 5,085,635 A | 2/1992 | Cragg | |
| 5,089,015 A | 2/1992 | Ross | |
| 5,132,473 A | 7/1992 | Furutaka et al. | |
| 5,141,494 A | 8/1992 | Danforth et al. | |
| 5,152,771 A | 10/1992 | Sabbaghian et al. | |
| 5,159,937 A | 11/1992 | Tremulis | |
| 5,161,547 A | 11/1992 | Tower | |
| 5,163,953 A | 11/1992 | Vince | |
| 5,167,628 A | 12/1992 | Boyles | |
| 5,209,741 A | 5/1993 | Spaeth | |
| 5,215,541 A | 6/1993 | Nashef et al. | |
| 5,217,483 A | 6/1993 | Tower | |
| 5,238,004 A | 8/1993 | Sahatjian et al. | |
| 5,258,023 A | 11/1993 | Reger | |
| 5,258,042 A | 11/1993 | Mehta | |
| 5,282,847 A | 2/1994 | Trescony et al. | |
| 5,295,958 A | 3/1994 | Shturman | |
| 5,332,402 A | 7/1994 | Teitelbaum | |
| 5,336,258 A | 8/1994 | Quintero et al. | |
| 5,350,398 A | 9/1994 | Pavcnik et al. | |
| 5,360,444 A | 11/1994 | Kusuhara | |
| 5,370,685 A | 12/1994 | Stevens | |
| 5,389,106 A | 2/1995 | Tower | |
| 5,397,351 A | 3/1995 | Pavcnik et al. | |
| 5,409,019 A | 4/1995 | Wilk | |
| 5,411,552 A | 5/1995 | Andersen et al. | |
| 5,425,762 A | 6/1995 | Muller | |
| 5,431,676 A | 7/1995 | Dubrul et al. | |
| 5,443,446 A | 8/1995 | Shturman | |
| 5,443,449 A | 8/1995 | Buelna | |
| 5,443,477 A | 8/1995 | Marin et al. | |
| 5,443,495 A | 8/1995 | Buscemi et al. | |
| 5,443,499 A | 8/1995 | Schmitt | |
| 5,476,506 A | 12/1995 | Lunn | |
| 5,476,510 A | 12/1995 | Eberhardt et al. | |
| 5,480,423 A | 1/1996 | Ravenscroft et al. | |
| 5,480,424 A | 1/1996 | Cox | |
| 5,500,014 A | 3/1996 | Quijano et al. | |
| 5,507,767 A | 4/1996 | Maeda et al. | |
| 5,534,007 A | 7/1996 | St. Germain et al. | |
| 5,545,133 A | 8/1996 | Burns et al. | |
| 5,545,209 A | 8/1996 | Roberts et al. | |
| 5,545,211 A | 8/1996 | An et al. | |
| 5,545,214 A | 8/1996 | Stevens | |

(56) References Cited

U.S. PATENT DOCUMENTS

| | | |
|---|---|---|
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |

(56) References Cited

U.S. PATENT DOCUMENTS

| | | |
|---|---|---|
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,892,292 B2 | 2/2011 | Stack et al. |
| 7,918,880 B2 | 4/2011 | Austin |
| 7,938,851 B2 | 5/2011 | Olson et al. |

(56) References Cited

U.S. PATENT DOCUMENTS

| | | |
|---|---|---|
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,696,737 B2 * | 4/2014 | Gainor ............... A61F 2/2418 623/1.24 |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 9,168,129 B2 * | 10/2015 | Valdez ............... A61F 2/2412 |
| 9,675,451 B2 * | 6/2017 | Garde ............... A61F 2/2409 |
| 9,895,225 B2 * | 2/2018 | Rolando ............ A61F 2/2445 |
| 9,974,649 B2 * | 5/2018 | Racchini ........... A61F 2/2418 |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |

(56) References Cited

U.S. PATENT DOCUMENTS

| | | |
|---|---|---|
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0275540 A1* | 11/2008 | Wen ............ A61F 2/2418 623/1.26 |

(56) References Cited

U.S. PATENT DOCUMENTS

| | | |
|---|---|---|
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0049313 A1 | 2/2010 | Alon et al. |
| 2010/0094399 A1 | 4/2010 | Dorn et al. |
| 2010/0121434 A1 | 5/2010 | Paul et al. |
| 2010/0191326 A1 | 7/2010 | Alkhatib |
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0123529 A1* | 5/2012 | Levi .................... A61F 2/2412 |
| | | 623/2.11 |
| 2012/0132547 A1 | 5/2012 | Salahieh et al. |
| 2012/0197379 A1 | 8/2012 | Laske et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0123796 A1 | 5/2013 | Sutton et al. |
| 2013/0158656 A1 | 6/2013 | Sutton et al. |
| 2013/0190865 A1 | 7/2013 | Anderson |
| 2013/0304199 A1* | 11/2013 | Sutton .................... A61F 2/2439 |
| | | 623/2.18 |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243966 A1* | 8/2014 | Garde .................... A61F 2/2409 |
| | | 623/2.18 |
| 2014/0243967 A1 | 8/2014 | Salahieh et al. |
| 2014/0277423 A1* | 9/2014 | Alkhatib .............. A61F 2/2418 |
| | | 623/2.38 |
| 2015/0005863 A1* | 1/2015 | Para .................... A61F 2/2418 |
| | | 623/1.2 |
| 2015/0142104 A1* | 5/2015 | Braido ................ A61F 2/2418 |
| | | 623/2.18 |
| 2017/0049566 A1* | 2/2017 | Zeng .................... A61F 2/2418 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1472996 A1 | 11/2004 |
| EP | 1229864 B1 | 4/2005 |
| EP | 1059894 B1 | 7/2005 |
| EP | 1078610 B1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |

(56) References Cited

FOREIGN PATENT DOCUMENTS

| | | |
|---|---|---|
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 4/2007 |
| WO | 2007058847 A2 | 5/2007 |
| WO | 2007092354 A2 | 8/2007 |
| WO | 2007097983 A2 | 8/2007 |
| WO | 2010042950 A2 | 4/2010 |
| WO | 2012116368 A2 | 8/2012 |
| WO | 2013009975 A1 | 1/2013 |
| WO | 2013028387 A2 | 2/2013 |
| WO | 2013096545 A1 | 6/2013 |
| WO | 2016126511 A2 | 8/2016 |

OTHER PUBLICATIONS

Atwood et al., "Insertion of Heart Valves by Catheterization." Project Supervised by Prof. S. Muftu of Northeastern University 2001-2002: 36-40, May 30, 2002.

Bodnar et al., "Replacement Cardiac Valves R Chapter 13: Extinct Cardiac Valve Prostheses." Pergamon Publishing Corporation. New York, 307-322, 1991.

Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.

Boudjemline et al., "Percutaneous Implantation of a Valve in the Descending Aorta in Lambs." Euro. Heart J., 23: 1045-1049, Jul. 2002.

Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.

Boudjemline et al., "Percutaneous Valve Insertion: A New Approach?" J. of Thoracic and Cardio. Surg, 125(3): 741-743, Mar. 2003.

Boudjemline et al., "Steps Toward Percutaneous Aortic Valve Replacement." Circulation, 105: 775-778, Feb. 12, 2002.

Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.

Cribier et al., "Percutaneous Transcatheter Implementation of an Aortic Valve Prosthesis for Calcitic Aortic Stenosis: First Human Case Description." Circulation, 106: 3006-3008, Dec. 10, 2002.

Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.

Ferrari et al., "Percutaneous Transvascular Aortic Valve Replacement with Self-Expanding Stent-Valve Device." Poster from the presentation given at SMIT 2000, 12th International Conference. Sep. 5, 2000.

Hijazi, "Transcatheter Valve Replacement: A New Era of Percutaneous Cardiac Intervention Begins." J. of Am. College of Cardio., 43(6): 1088-1089, Mar. 17, 2004.

Huber et al., "Do Valved Stents Compromise Coronary Flow?" European Journal of Cardio-thoracic Surgery, vol. 25: 754-759, Jan. 23, 2004.

Knudsen et al., "Catheter-implanted prosthetic heart valves." Int'l J. of Art. Organs, 16(5): 253-262, May 1993.

Kort et al., "Minimally Invasive Aortic Valve Replacement: Echocardiographic and Clinical Results." Am. Heart J., 142(3): 476-481, Sep. 2001.

Love et al., The Autogenous Tissue Heart Valve: Current Status. Journal of Cardiac Surgery, 6(4): 499-507, Mar. 1991.

Lutter et al., "Percutaneous Aortic Valve Replacement: An Experimental Study. I. Studies on Implantation." J. of Thoracic and Cardio. Surg., 123(4): 768-776, Apr. 2002.

Moulopoulos et al., "Catheter-Mounted Aortic Valves." Annals of Thoracic Surg., 11(5): 423-430, May 1971.

Paniagua et al., "Percutaneous Heart Valve in the Chronic in Vitro Testing Model." Circulation, 106: e51-e52, Sep. 17, 2002.

Paniagua et al., "Heart Watch." Texas Heart Institute. Edition: 8 pages, Spring, 2004.

Pavcnik et al., "Percutaneous Bioprosthetic Venous Valve: A Long-term Study in Sheep." J. of Vascular Surg., 35(3): 598-603, Mar. 2002.

Phillips et al., "A Temporary Catheter-Tip Aortic Valve: Hemodynamic Effects on Experimental Acute Aortic Insufficiency." Annals of Thoracic Surg., 21(2): 134-136, Feb. 1976.

Sochman et al., "Percutaneous Transcatheter Aortic Disc Valve Prosthesis Implantation: A Feasibility Study." Cardiovasc. Intervent. Radiol., 23: 384-388, Sep. 2000.

Stuart, "In Heart Valves, A Brave, New Non-Surgical World." Start-Up. Feb. 9-17, 2004.

Vahanian et al., "Percutaneous Approaches to Valvular Disease." Circulation, 109: 1572-1579, Apr. 6, 2004.

Van Herwerden et al., "Percutaneous Valve Implantation: Back to the Future?" Euro. Heart J., 23(18): 1415-1416, Sep. 2002.

Zhou et al, "Self-expandable Valved Stent of Large Size: Off-Bypass Implantation in Pulmonary Position." Eur. J. Cardiothorac, 24: 212-216, Aug. 2003.

Examiner's First Report on AU Patent Application No. 2011202667, dated May 17, 2012.

"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.

Atwood et al., "Insertion of Heart Valves by Catheterization." The Capstone Design Course Report. MIME 1501-1502. Technical Design Report. Northeastern University, pp. 1-93, Nov. 5, 2007.

Supplemental Search Report from EP Patent Office, EP Application No. 04813777.2, dated Aug. 19, 2011.

Supplemental Search Report from EP Patent Office, EP Application No. 04815634.3, dated Aug. 19, 2011.

Cunanan et al., "Tissue Characterization and Calcification Potential of Commercial Bioprosthetic Heart Valves." Ann. Thorac. Surg., S417-421, May 15, 2001.

Cunliffe et al., "Glutaraldehyde Inactivation of Exotic Animal Viruses in Swine Heart Tissue." Applied and Environmental Microbiology, Greenport, New York, 37(5): 1044-1046, May 1979.

(56) References Cited

OTHER PUBLICATIONS

EP Search Report for EP Application No. 06824992.9, dated Aug. 10, 2011.

"Heart Valve Materials—Bovine (cow)." Equine & Porcine Pericardium, Maverick Biosciences Pty. Lt, http://maverickbio.com/biological-medical-device-materials.php?htm. 2009.

Helmus, "Mechanical and Bioprosthetic Heart Valves in Biomaterials for Artificial Organs." Woodhead Publishing Limited: 114-162, 2011.

Hourihan et al., "Transcatheter Umbrella Closure of Valvular and Paravalvular Leaks." JACC, Boston, Massachusetts, 20(6): 1371-1377, Nov. 15, 1992.

Laborde et al., "Percutaneous Implantation of the Corevalve Aortic Valve Prosthesis for Patients Presenting High Risk for Surgical Valve Replacement." EuroIntervention: 472-474, Feb. 2006.

Levy, "Mycobacterium Chelonei Infection of Porcine Heart Valves." The New England Journal of Medicine, Washington DC, 297(12), Sep. 22, 1977.

Supplemental Search Report from EP Patent Office, EP Application No. 05758878.2, dated Oct. 24, 2011.

"Pericardial Heart Valves." Edwards Lifesciences, Cardiovascular Surgery FAQ, http://www.edwards.com/products/cardiovascularsurgeryfaq.htm, Nov. 14, 2010.

Southern Lights Biomaterials Homepage, http://www.slv.co.nz/, Jan. 7, 2011.

Stassano. "Mid-term Results of the Valve-on-Valve Technique for Bioprosthetic Failure." European Journal of Cardiothoracic Surgery: vol. 18, 453-457, Oct. 2000.

Topol. "Percutaneous Expandable Prosthetic Valves." Textbook of Interventional Cardiology, W.B. Saunders Company, 2: 1268-1276, 1994.

Invite to Pay Additional Fees and, Where Applicable, Protest Fee, PCT/US2016/045335, dated Nov. 14, 2016.

\* cited by examiner

REPLACEMENT HEART VALVE IMPLANT

CROSS-REFERENCE TO RELATED APPLICATIONS

This application claims the benefit of U.S. Provisional Application No. 62/204,073, filed Aug. 12, 2015.

TECHNICAL FIELD

The present disclosure pertains to medical devices, and methods for manufacturing and/or using medical devices. More particularly, the present disclosure pertains to configurations of a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a replacement heart valve implant may comprise a braided anchor member configured to actuate between an elongated delivery configuration and an expanded deployed configuration, the braided anchor member formed from a plurality of filaments, a circumferential seal member disposed about a distal portion of the braided anchor member, the circumferential seal member including a reinforcing band disposed at a distal end thereof, and a plurality of valve leaflets connected to the braided anchor member. The reinforcing band is secured to the braided anchor member adjacent a distal end of the braided anchor member by a plurality of lashings, wherein each lashing is attached to two individual filaments of the plurality of filaments.

In addition or alternatively, and in a second aspect, the two individual filaments are crossing each other where each lashing is attached thereto.

In addition or alternatively, and in a third aspect, the two individual filaments are immediately adjacent each other where each lashing is attached thereto.

In addition or alternatively, and in a fourth aspect, at least a portion of the braided anchor member extends distally of the plurality of lashings.

In addition or alternatively, and in a fifth aspect, at least a portion of the braided anchor member extends distally of all of the plurality of lashings.

In addition or alternatively, and in a sixth aspect, at least a portion of each of the two filaments extends distally of each lashing attached thereto.

In addition or alternatively, and in a seventh aspect, each lashing comprises more than one suture member.

In addition or alternatively, and in an eighth aspect, the reinforcing band includes a fabric strip.

In addition or alternatively, and in a ninth aspect, each of the plurality of valve leaflets is secured directly to the reinforcing band.

In addition or alternatively, and in a tenth aspect, a replacement heart valve implant may comprise a braided anchor member configured to actuate between an elongated delivery configuration and an expanded deployed configuration, the braided anchor member formed from a plurality of filaments defining a body section, a proximal crown section, and a distal crown section, a circumferential seal member disposed about a distal portion of the braided anchor member, the circumferential seal member including a reinforcing band disposed at a distal end thereof, and a plurality of valve leaflets connected to the braided anchor member. The proximal crown section may include a first plurality of end loops and a second plurality of end loops. A proximalmost extent of the first plurality of end loops and the second plurality of end loops varies around a circumference of the braided anchor member.

In addition or alternatively, and in an eleventh aspect, when the braided anchor member is in the deployed configuration the first plurality of end loops extends proximally to a first proximal extent and the second plurality of end loops extends proximally to a second proximal extent distal of the first proximal extent.

In addition or alternatively, and in a twelfth aspect, the braided anchor member includes a plurality of buckle members fixedly attached thereto, the plurality of buckle members being configured to lock the braided anchor member in the deployed configuration.

In addition or alternatively, and in a thirteenth aspect, each of the plurality of buckle members is positioned circumferentially between adjacent end loops from the first plurality of end loops.

In addition or alternatively, and in a fourteenth aspect, each of the plurality of buckle members is positioned circumferentially over one of the second plurality of end loops.

In addition or alternatively, and in a fifteenth aspect, two of the first plurality of end loops and two of the second plurality of end loops is disposed circumferentially between adjacent buckle members.

In addition or alternatively, and in a sixteenth aspect, when the braided anchor member is in the elongated delivery configuration the first plurality of end loops extends farther proximally than the second plurality of end loops.

In addition or alternatively, and in a seventeenth aspect, the distal crown section includes a third plurality of end loops and a fourth plurality of end loops; wherein a distalmost extent of the third plurality of end loops and the fourth plurality of end loops varies around a circumference of the braided anchor member.

In addition or alternatively, and in an eighteenth aspect, when the braided anchor member is in the deployed configuration the third plurality of end loops extends distally to a first distal extent and the fourth plurality of end loops extends distally to a second distal extent proximal of the first distal extent.

In addition or alternatively, and in a nineteenth aspect, when the braided anchor member is in the elongated delivery configuration the third plurality of end loops extends farther distally than the fourth plurality of end loops.

In addition or alternatively, and in a twentieth aspect, the braided anchor member is formed from a metallic material.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
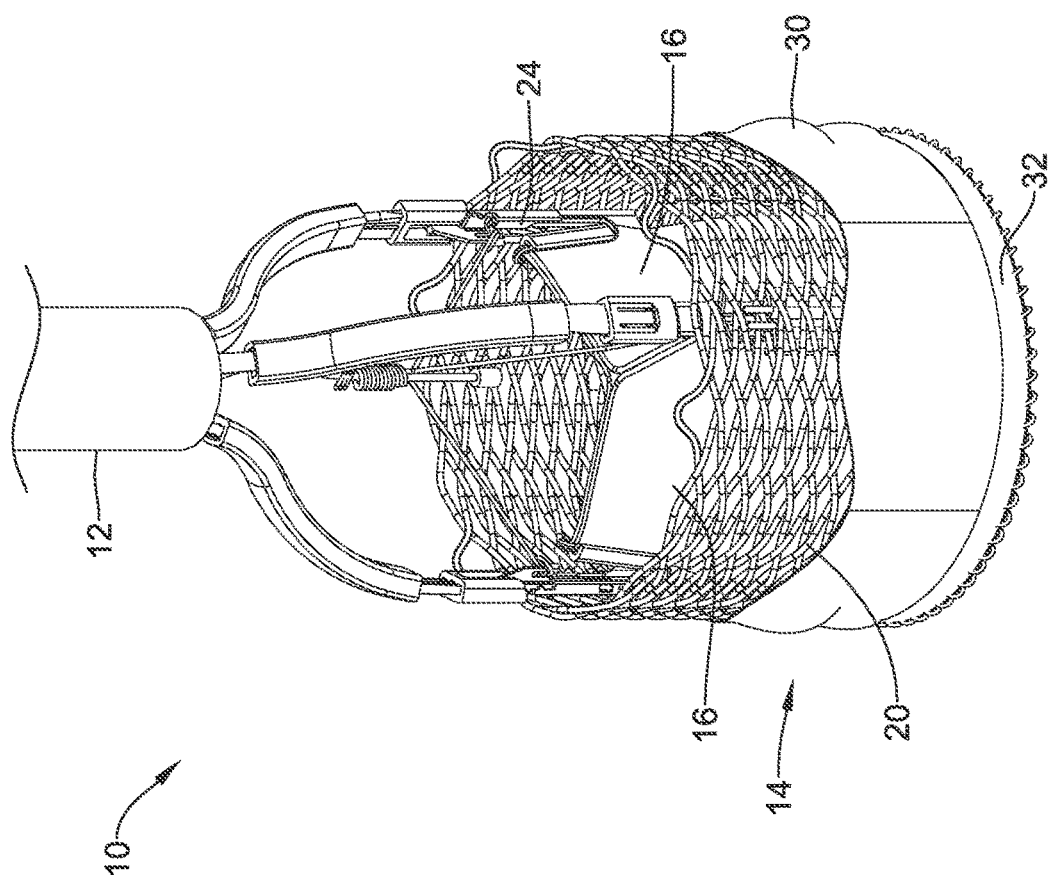
FIG. 1 illustrates an example medical implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 illustrates a portion of an example medical implant 14. It should be noted that some features of the medical implant 14 are either not shown, or are shown schematically, in FIG. 1 for simplicity. Additional details regarding some of the components of the medical implant 14 may be provided in other figures in greater detail. In some embodiments, a medical implant 14 may be a replacement heart valve implant. In some embodiments, a medical implant 14 (i.e., a replacement heart valve, for example, which term may be used interchangeably with the term "medical implant" herein) may be coupled to a delivery system 12 and/or disposed within a lumen of the delivery system 12 during delivery of the medical implant 14. In some embodiments, a handle may be disposed at a proximal end of the delivery system 12, and may include one of more actuation means associated therewith. In general, the handle may be configured to manipulate the position of the delivery system 12 and/or aid in the deployment of the medical implant 14.

Figure 2:
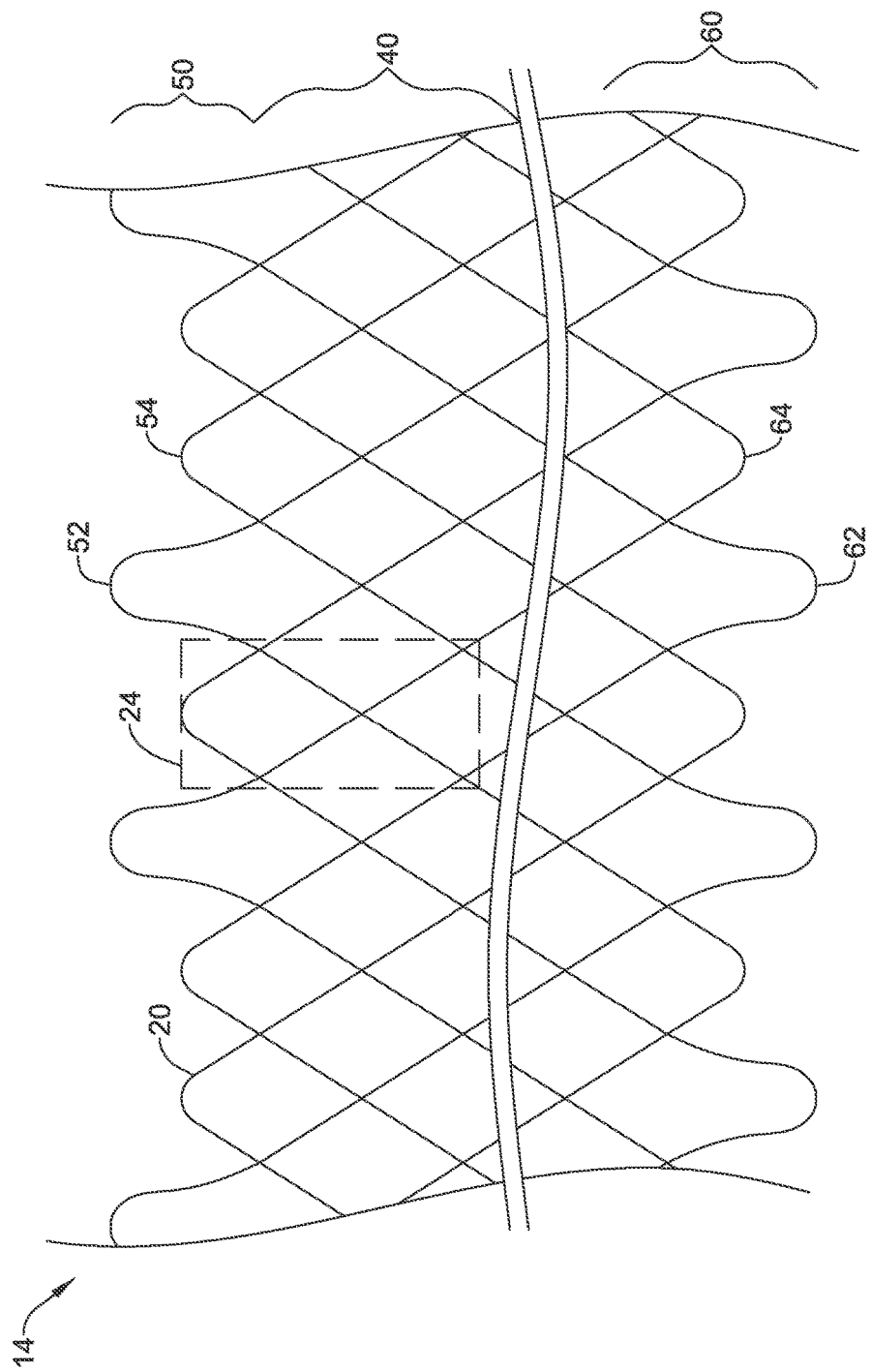
FIG. 2 illustrates selected portions of an example medical implant in a delivery configuration.
Figure 3:
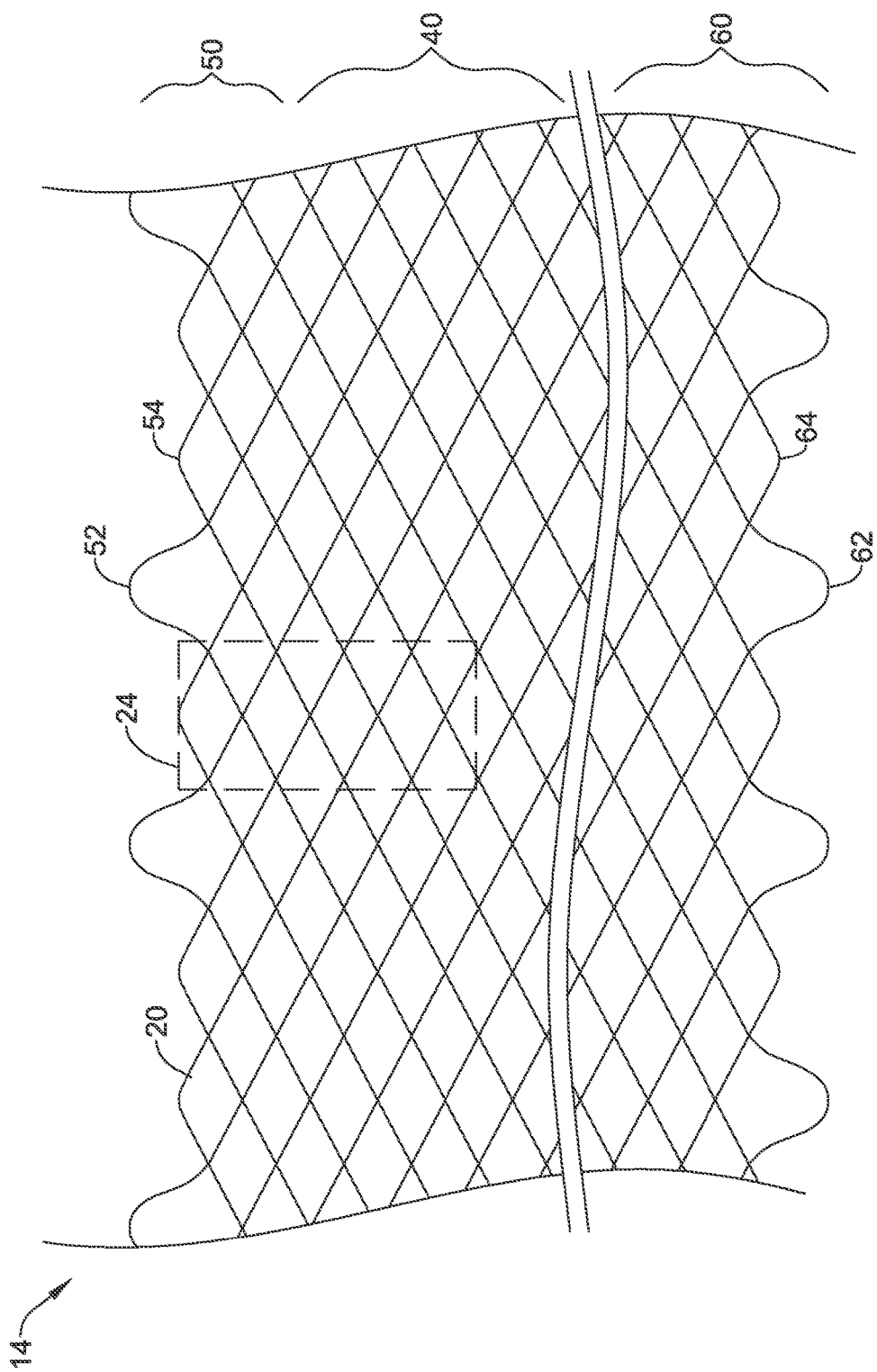
FIG. 3 illustrates selected portions of an example medical implant in a deployed configuration.

In use, the medical implant 14 may be advanced percutaneously through the vasculature to a position adjacent to an area of interest. For example, the medical implant 14 may be advanced through the vasculature and across the aortic arch to a position adjacent to a defective aortic valve. Alternative approaches to treat a defective aortic valve or other heart valve(s) are also contemplated with the medical implant 14. During delivery, the medical implant 14 may be generally disposed in an elongated and low profile "delivery" configuration within the delivery system 12. A portion of the medical implant 14 may be seen schematically in the "delivery" configuration in FIG. 2 for example. Once positioned, the delivery system 12 may be retracted relative to the medical implant 14 to expose the medical implant 14. In some embodiments, the medical implant 14 may be actuated using the handle in order to translate the medical implant 14 into a generally shortened and larger profile "deployed" configuration suitable for implantation within the anatomy (as shown in FIGS. 1 and 3, for example). When the medical implant 14 is suitably deployed within the anatomy, the delivery system 12 can be disconnected from the medical implant 14 and the delivery system 12 removed from the vasculature, leaving the medical implant 14 in place in a "released" configuration to function as, for example, a suitable replacement for the native aortic valve. In at least some interventions, the medical implant 14 may be deployed within the native valve (e.g., the native valve is left in place and not excised). Alternatively, the native valve may be removed and the medical implant 14 may be deployed in its place as a replacement.

FIG. 1 illustrates some selected components of an example medical implant 14 in the deployed configuration. For example, here it can be seen that the medical implant 14 may include a plurality of valve leaflets 16 (e.g., bovine pericardial) which may be connected and/or secured to a braided anchor member 20 formed from a plurality of filaments. In some embodiments, the braided anchor member 20 may be reversibly actuatable between an elongated "delivery" configuration and an expanded "deployed" configuration. In at least some embodiments, the "delivery" and "deployed" configurations of the braided anchor member 20 and the medical implant 14 may be considered substantially the same and/or interchangeable. In other words, the configuration of one of these elements may be indicative and/or representative of the other of these elements being in the same configuration. That is, if the medical implant is in the "deployed" configuration, the braided anchor member 20 may also be in the "deployed" configuration and vice-versa. Similarly, if the medical implant is in the "delivery" configuration, the braided anchor member 20 may also be in the "delivery" configuration and vice-versa.

In some embodiments, the braided anchor member 20 may be substantially cylindrical and/or tubular in shape or configuration. In some embodiments, the braided anchor member 20 may define a central longitudinal axis extending therethrough along a fluid flow path through the medical implant 14. Other shapes and/or configurations are also contemplated. Some suitable but non-limiting materials for the braided anchor member 20, for example metallic materials or polymeric materials, may be described below.

In some embodiments, the plurality of filaments of the braided anchor member 20 may include at least two individual filaments. In some embodiments, the plurality of filaments may define a body section 40, a proximal crown section 50, and a distal crown section 60. In some embodiments, the proximal crown section 50 and the distal crown section 60 may be constructed and/or configured in a substantially similar arrangement. In some embodiments, the proximal crown section 50 and the distal crown section 60 may be constructed and/or configured in a substantially different arrangement. In some embodiments, one or both of the proximal crown section 50 and the distal crown section 60 may be constructed and/or configured in a substantially uniform and/or regular arrangement.

In some embodiments, the proximal crown section 50 may include a first plurality of end loops 52 and a second plurality of end loops 54. In some embodiments, a proximalmost extent of the first plurality of end loops 52 and a proximalmost extent of the second plurality of end loops 54 varies around a circumference of the braided anchor member 20. In some embodiments, when the braided anchor member 20 is in the "deployed" configuration, the first plurality of end loops 52 may extend proximally to a first proximal extent and the second plurality of end loops 54 may extend proximally to a second proximal extent distal of the first proximal extent, as seen in FIG. 3 for example. In some embodiments, when the braided anchor member 20 is in the "delivery" configuration, the first plurality of end loops 52 may extend farther proximally than the second plurality of end loops 54, as seen in FIG. 2 for example.

In some embodiments, the distal crown section 60 may include a third plurality of end loops 62 and a fourth plurality of end loops 64. In some embodiments, a distalmost extent of the third plurality of end loops 62 and a distalmost extent of the fourth plurality of end loops 64 varies around a circumference of the braided anchor member 20. In some embodiments, when the braided anchor member 20 is in the "deployed" configuration, the third plurality of end loops 62 may extend distally to a first distal extent and the fourth plurality of end loops 64 may extend distally to a second distal extent proximal of the first distal extent, as seen in FIG. 3 for example. In some embodiments, when the braided anchor member 20 is in the "delivery" configuration, the third plurality of end loops 62 may extend farther distally than the fourth plurality of end loops 64, as seen in FIG. 2 for example.

In some embodiments, the medical implant 14 may include a plurality of locking mechanisms configured to secure the braided anchor member 20 in the "deployed" configuration. In some embodiments, the plurality of locking mechanisms may each include a buckle member 24 fixedly attached to the braided anchor member 20 and a post member axially translatable relative to the buckle member 24. In some embodiments, the braided anchor member 20 includes a plurality of buckle members 24 fixedly attached thereto. In some embodiments, the plurality of buckle members 24 may be configured to lock the braided anchor member 20 in the "deployed" configuration. In some embodiments, each of the plurality of buckle members 24 may be positioned circumferentially between adjacent end loops from the first plurality of end loops 52. In some embodiments, each of the plurality of buckle members 24 may be positioned circumferentially over one of the second plurality of end loops 54. In some embodiments, two of the first plurality of end loops 52 and two of the second plurality of end loops 54 may be disposed circumferentially between adjacent buckle members 24.

In some embodiments, at least one actuator member may be configured to engage with the plurality of locking mechanisms and actuate the braided anchor member 20 between the "delivery" configuration and the "deployed" configuration. In some embodiments, one actuator member may correspond to, engage with, and/or actuate one locking mechanism. In some embodiments, one actuator member may correspond to, engage with, and/or actuate more than one locking mechanism. Other configurations are also contemplated.

While a plurality of actuator members, buckle members, post members, other elements, and/or corresponding locking mechanisms may be included in a medical implant 14, for clarity and brevity, much of the following discussion will be limited to a single instance of these elements. The skilled person will readily recognize that the features and operation of the examples discussed below may apply equally to and across all instances of the disclosed elements (i.e., each locking mechanism, each actuator member, each post member, etc.). Some suitable but non-limiting materials for locking mechanisms, the actuator members, the buckle members, the post members, etc., for example metallic materials or polymeric materials, may be described below.

In some embodiments, the plurality of locking mechanisms may each comprise an axially movable post member, for example at the commissure portions of the valve leaflets 16 (post member may sometimes be referred to as a "commissure post", which may include one or more of the plurality of valve leaflets 16 secured thereto), and a buckle member 24 fixedly attached to the braided anchor member 20. In other words, in at least some embodiments, a medical implant 14 may include a plurality of post members and a corresponding plurality of buckle members 24. Other configurations and correspondences are also contemplated.

In some embodiments, the post member may be configured to engage with the buckle member 24 to lock the braided anchor member 20 in the "deployed" configuration. In some embodiments, the post member may engage the buckle member 24 in the "deployed" configuration, and consequently, in the "released" configuration. In some embodiments, the post member may be axially and/or longitudinally spaced apart from the buckle member 24 in the "delivery" configuration. Some suitable but non-limiting materials for the post member and/or the buckle member 24, for example metallic materials or polymeric materials, may be described below.

In some embodiments, a distal end of the axially movable post member may be secured and/or attached (i.e., fixedly attached, movably attached, removably attached, etc.) to a distal portion of the braided anchor member 20, such as by a suture, a tether, adhesives, or other suitable element. In some embodiments, the post member may be movable relative to the braided anchor member 20, and the buckle member 24. In some embodiments, the post member may be axially or longitudinally movable relative to the braided anchor member 20, and the buckle member 24. In some embodiments, the buckle member 24 may be fixedly attached to the braided anchor member 20. Other embodiments are contemplated where the buckle member 24 may be movably or removably attached to the braided anchor member 20. In some embodiments, the post member may be fixedly attached to the braided anchor member 20 and the buckle member 24 may be fixedly attached to the braided anchor member 20. In some embodiments, one of the post member and the buckle member 24 may be fixedly attached to the braided anchor member 20 and the other may be movably or removably attached to the braided anchor member 20. In some embodiments, the post member may be secured or attached (i.e., fixedly attached, movably attached, removably attached, etc.) to a distal end of the braided anchor member 20. In some embodiments, the buckle member 24 may be fixed or attached to a proximal portion of the braided anchor member 20. In some embodiments, the buckle member 24 may be fixed or attached at or to a proximal end of the braided anchor member 20.

In some embodiments, the medical implant 14 may include one or more of the plurality of valve leaflets 16 secured to the braided anchor member 20 at, adjacent to, and/or using (at least in part) individual, corresponding post members. In some embodiments, the plurality of valve leaflets 16 may also be secured to a base, or the distal end, of the braided anchor member 20. In some embodiments, the plurality of valve leaflets 16 may be coupled and/or secured (i.e., to the post member, to the braided anchor member 20, and/or back to themselves) using one or more sutures, threads, wires, filaments, or other suitable elements. In some embodiments, the plurality of valve leaflets 16 may be coupled and/or secured (i.e., to the post member, to the braided anchor member 20, and/or back to themselves) using an adhesive, a bonding agent, or other suitable securing means. In some embodiments, the plurality of valve leaflets 16 may be coupled and/or secured (i.e., to the post member, to the braided anchor member 20, and/or back to themselves) using a fabric strip, a textile, or other thin flexible material.

In some embodiments, the braided anchor member 20 may have a total of three buckle members 24 and three post members attached and/or secured thereto. Similarly, one actuator member may be operatively associated with each post member and buckle member 24, for a total of three actuator members in the illustrated examples. Other embodiments are contemplated where fewer or more buckle members 24, post members, actuator members, etc. may be utilized.

In some embodiments, a circumferential seal member 30 may be disposed about the braided anchor member 20 and, as the term suggests, may help to seal an exterior of the medical implant 14 within and/or against a target site or area of interest upon deployment, thereby preventing leakage around the medical implant 14. In some embodiments, the circumferential seal member 30 may be disposed about the braided anchor member 20. In some embodiments, the circumferential seal member 30 may be disposed around a perimeter and/or on or against an exterior surface of the braided anchor member 20. In some embodiments, the circumferential seal member 30 may be coupled and/or secured to the braided anchor member 20.

In some embodiments, the circumferential seal member 30 may include a plurality of layers of polymeric material. For example, in some embodiments, a radially innermost layer may comprise a polycarbonate and a polyurethane; a radially outermost layer may comprise a polycarbonate and a polyurethane; at least one inner layer disposed between the radially outermost layer and the radially innermost layer may comprise a polycarbonate and a polyurethane. These are only examples. Other suitable polymeric materials are also contemplated. Some suitable polymeric materials may include, but are not necessarily limited to, polyamide, polyether block amide, polyethylene, polyethylene terephthalate, polypropylene, polyvinylchloride, polytetrafluoroethylene, polysulfone, and copolymers, blends, mixtures or combinations thereof.

In some embodiments, the modulus of elasticity of the inner layer may be less than the modulus of elasticity of the radially innermost outer layer and/or the modulus of elasticity of the radially outermost outer layer. In other embodiments, the elongation to break of the inner layer may be greater than the elongation to break of the radially innermost outer layer and/or the elongation to break of the radially outermost outer layer. Although the radially innermost outer layer and the radially outermost outer layer may comprise the same material, it will be appreciated that they may be compositionally the same or different. In addition to the radially innermost outer layer, the at least one inner layer, and the radially outermost outer layer, the circumferential seal member 30 may also include a reinforcement, a reinforcing layer, and/or one or more reinforcing members added to the polymeric material prior to curing. The reinforcement, the reinforcing layer, and/or the one or more reinforcing members may comprise a woven or nonwoven fabric and may be positioned within or between the various layers. In some embodiments, the reinforcement, the reinforcing layer, and/or the one or more reinforcing members may be positioned on a radially innermost surface or radially outermost surface of the circumferential seal member 30. In some embodiments, the reinforcement, the reinforcing layer, and/or the one or more reinforcing members may be generally aligned. In some embodiments, the reinforcement, the reinforcing layer, and/or the one or more reinforcing members may be randomly oriented and/or disposed on the circumferential seal member 30.

In some embodiments, the circumferential seal member 30 may include a reinforcing band 32 disposed at a distal end thereof. In some embodiments, the reinforcing band 32 may be integrally formed with, incorporated into, adhered to, and/or at least partially embedded in the circumferential seal member 30. In some embodiments, the reinforcing band 32 may be formed from a woven or nonwoven fabric strip, a textile, or other thin flexible material. The reinforcing band 32 may provide tear resistance in the vicinity of sutures or other attachment elements associated with components or aspects of the medical implant 14.

Figure 4:
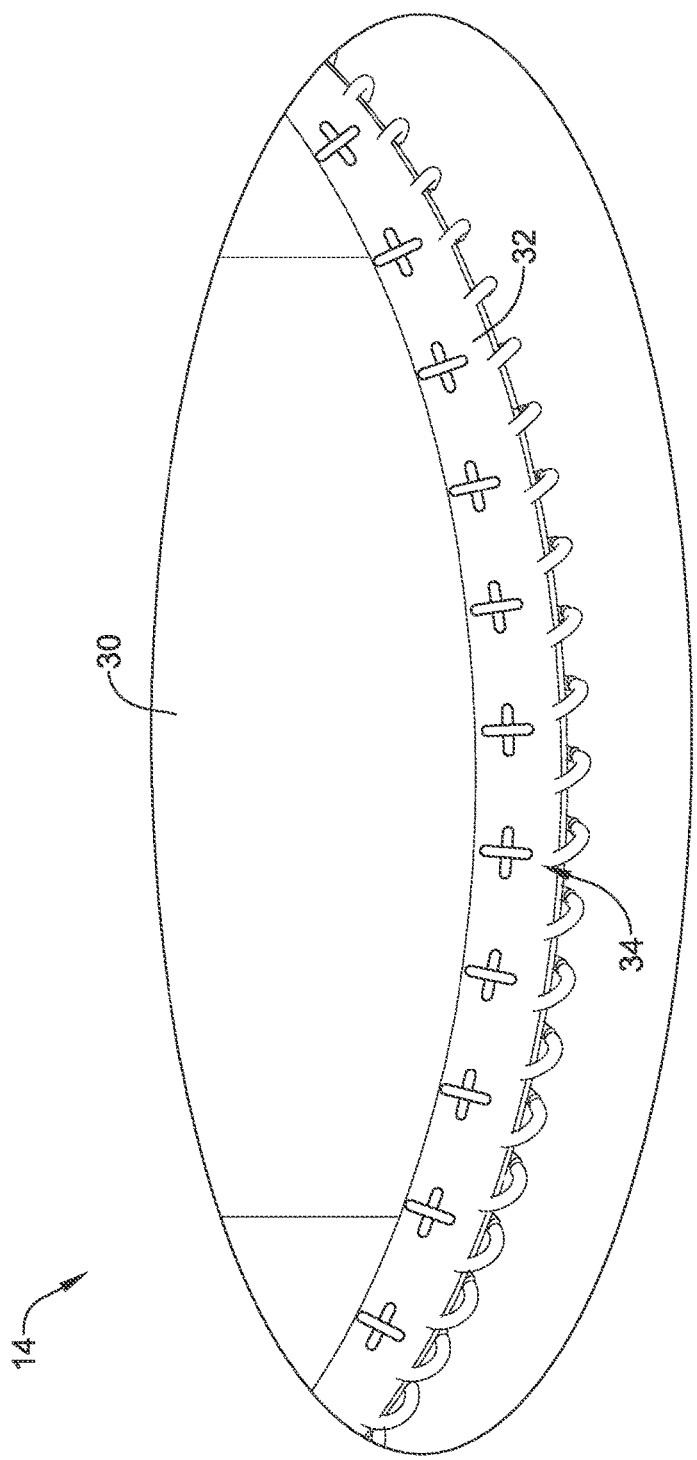
FIG. 4 illustrates selected portions of an example medical implant.
Figure 5:
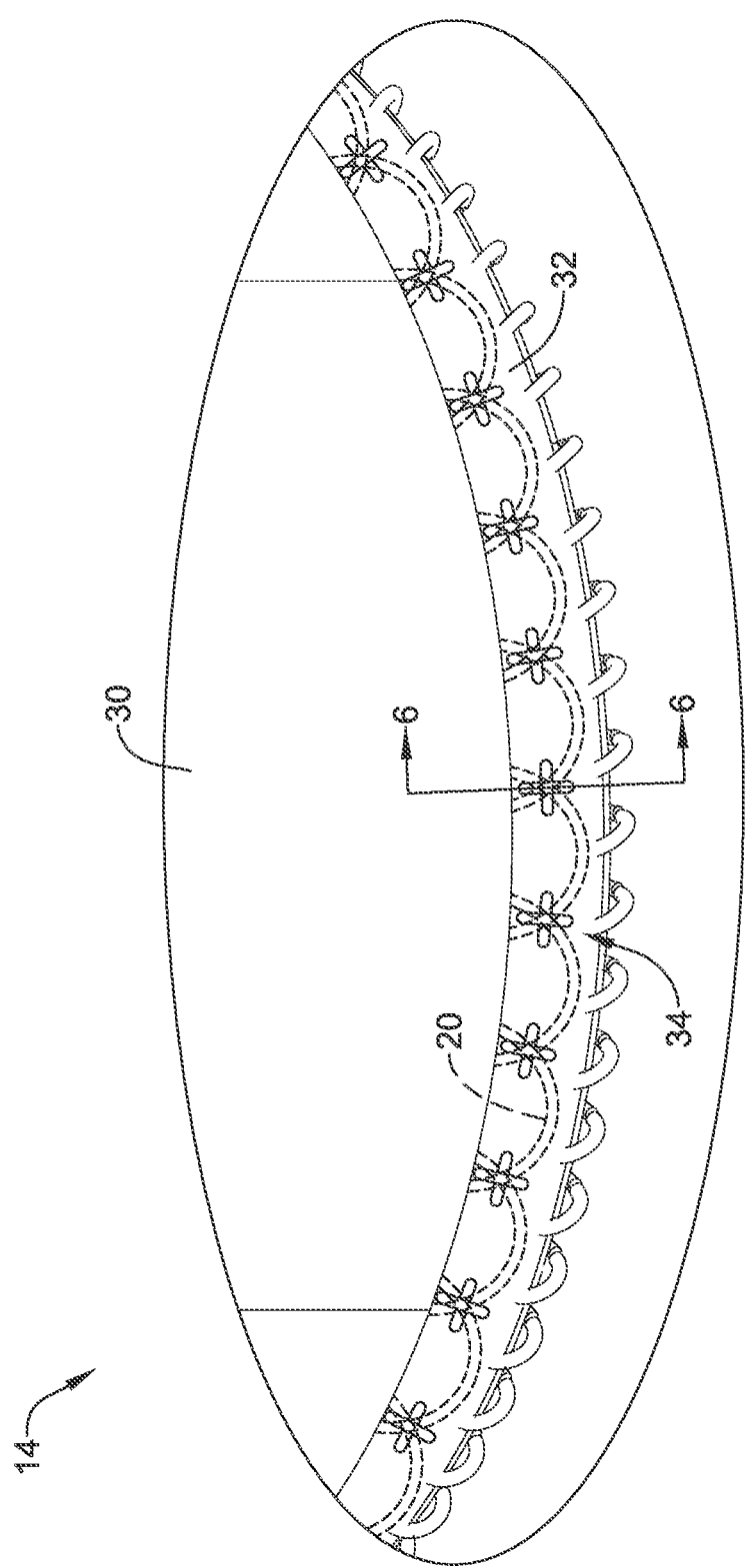
FIG. 5 illustrates selected portions of an example medical implant.
Figure 6:
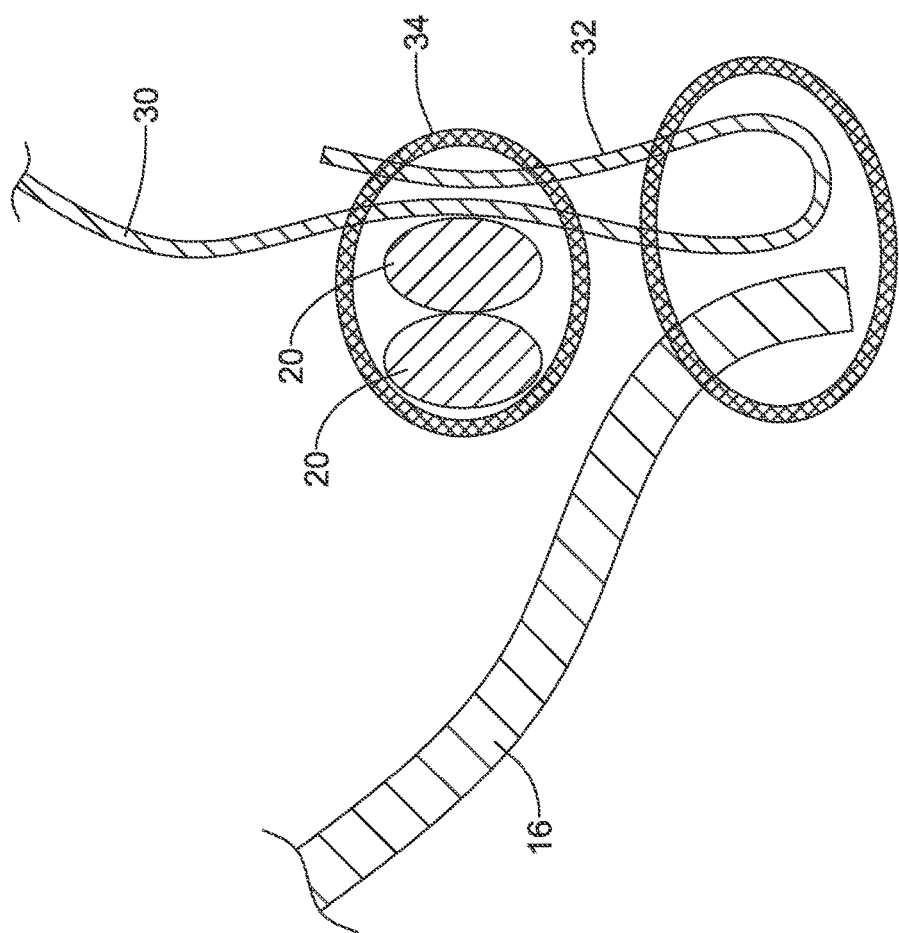
FIG. 6 is a partial section view of selected portions of an example medical implant.

In some embodiments, the reinforcing band 32 may be secured to the braided anchor member 20 adjacent a distal end of the braided anchor member 20 by a plurality of lashings 34, as seen in FIG. 4 for example. In some embodiments, each lashing 34 may be attached to two distinct segments of the braided anchor member 20. In some embodiments, each lashing 34 may be attached and/or secured to two individual filaments of the plurality of filaments of the braided anchor member 20, as seen in FIG. 5 for example. In some embodiments, the two individual filaments of the plurality of filaments may be crossing each other where each lashing 34 is attached thereto, as seen in FIG. 5 for example. In some embodiments, the two individual filaments of the plurality of filaments may be immediately adjacent each other where each lashing 34 is attached thereto, as seen in FIG. 6 for example. In some embodiments, each lashing 34 may be directly attached to two distinct segments of the braided anchor member 20. In some embodiments, each lashing 34 may be directly attached and/or secured to two individual filaments of the plurality of filaments of the braided anchor member 20, as seen in FIG. 5 for example.

In some embodiments, at least a portion of the braided anchor member 20 extends distally of the plurality of lashings 34. In some embodiments, at least a portion of the distal crown section 60 extends distally of the plurality of lashings 34. In some embodiments, at least a portion of the braided anchor member 20 extends distally of all of the plurality of lashing 34. In some embodiments, at least a portion of each of the two individual filaments of the plurality of filaments extends distally of each lashing 34 attached thereto. In some embodiments, each of the plurality of lashings 34 includes a suture member. In some embodiments, each of the plurality of lashings 34 includes more than one suture member.

In some embodiments, each one of the plurality of valve leaflets 16 may be secured directly to the reinforcing band 32 as a means of securing the plurality of valve leaflets to the distal end of the braided anchor member 20. In some embodiments, the plurality of valve leaflets 16 may not be secured directly to the braided anchor member 20. In some embodiments, the reinforcing band 32 may include a plurality of perforations extending through the reinforcing band 32 and/or the circumferential seal member 30. In some embodiments, the plurality of perforations may accommodate sutures passing therethrough to secure elements or aspects of the medical implant 14, such as (but not limited to) the plurality of valve leaflets 16, for example.

In some embodiments, a buckle member 24 may permit an actuator member and/or a post member to be slidably received within and/or axially translate axially through the channel. In some embodiments, the buckle member 24 may be configured to prevent the actuator member and/or the post member from exiting the buckle member 24 in a radially inward direction toward the central longitudinal axis of the braided anchor member 20, thereby limiting motion of the actuator member and/or the post member within the braided anchor member 20 to axial translation.

In some embodiments, an example post member may include a proximal end and a distal end. In some embodiments, the post member may include a body portion extending generally along a first plane. In some embodiments, when the post member is engaged with the buckle member 24, the first plane may be oriented generally parallel to an inside surface of the back wall of the buckle member 24. In some embodiments, the post member may include a latch portion connected to and/or integrally formed with or as a part of the body portion. In some embodiments, the latch portion may be configured to be deflected by the buckle member 24 as the post member is translated proximally through the buckle member 24. In some embodiments, the post member may be axially translatable relative to the buckle member 24.

In some embodiments, the post member may include a cantilevered leg connected by a flexible hinge portion at the distal end of the post member. In some embodiments, the cantilevered leg may extend proximally from the hinge portion and/or the distal end to a free end of the cantilevered leg disposed radially inward from the body portion and/or the latch portion (relative to the braided anchor member 20).

In some embodiments, the hinge portion may have and/or include a radius of curvature. For example, in some embodiments, the radius of curvature may be between 0 and 3 millimeters (mm). In some embodiments, the radius of curvature may be an inner radius of curvature of between 0 and 3 millimeters (mm). In some embodiments, the radius of curvature may be an outer radius of curvature of between 0 and 3 millimeters (mm). Other configurations and radii of curvature are also contemplated. In some embodiments, the hinge portion may be configured to dispose the body portion and the cantilevered leg at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion flexibly attaches the cantilevered leg to the body portion of the post member. In some embodiments, at least part of the cantilevered leg may longitudinally overlap the buckle member 24 along a central longitudinal axis of the braided anchor member 20 in the "deployed" configuration.

In some embodiments, the cantilevered leg may include a free end and a secured end, where the cantilevered leg may be attached to the body portion of the post member at the secured end, which may connect directly to the hinge portion. In some embodiments, the free end of the cantilevered leg may be unattached (i.e., not directly attached) to any other structure of the medical implant 14, except for the cantilevered leg 84 and/or the plurality of valve leaflets 16. In other words, in some embodiments, the free end may not be directly attached to any other structure or feature of the medical implant 14 (i.e., the buckle member 24, the braided anchor member 20, etc.). In some embodiments, a distalmost end of the post member, which in at least some embodiments may be and/or include the hinge portion, may be coupled to the distal end of the braided anchor member 20, such as, for example, by a fastening element such as a suture, a filament, a wire, or other suitable means. In some embodiments, the body portion may include one or more apertures or holes for securing the post member to the braided anchor member 20 using a fastening element, such as a suture, for example. As such, when the post member is pulled proximally to engage the buckle member 24, the distal end of the braided anchor member 20 is also pulled proximally relative to the buckle member 24, thereby transitioning from the "delivery" configuration of FIG. 2 toward the "deployed" configuration of FIG. 3.

In at least some embodiments, one or more of the plurality of valve leaflets 16 may be attached to the cantilevered leg(s). In some embodiments, attachment of the plurality of valve leaflets 16 to the cantilevered leg(s) may provide flexibility and/or a reduction in stress between the plurality of valve leaflets 16 and the braided anchor member 20. In some embodiments, at least a portion of the plurality of valve leaflets 16 may axially or longitudinally overlap at least a portion of the buckle members 24 at a common position along a central longitudinal axis of the braided anchor member 20, which in some embodiments may allow for a shorter overall length or height of the medical implant 14. In some embodiments, the plurality of valve leaflets 16 may be secured directly to the cantilevered leg(s). In some embodiments, the plurality of valve leaflets 16 may not be directly secured to the body portion of the post member, but is instead coupled to the post member via the cantilevered leg(s). In some embodiments, the plurality of valve leaflets 16 may be wrapped around at least a portion of the cantilevered leg(s). In some embodiments, a distalmost end of the plurality of valve leaflets 16 may be coupled to the distal end of the braided anchor member 20. In some embodiments, the plurality of valve leaflets 16 may be coupled and/or secured (i.e., to the cantilevered leg, to the braided anchor member 20, and/or back to themselves) using one or more sutures, threads, wires, filaments, or other suitable elements. In some embodiments, the plurality of valve leaflets 16 may be coupled and/or secured (i.e., to the cantilevered leg, to the braided anchor member 20, and/or back to themselves) using an adhesive, a bonding agent, or other suitable securing means. In some embodiments, the plurality of valve leaflets 16 may be coupled and/or secured (i.e., to the cantilevered leg, to the braided anchor member 20, and/or back to themselves) using a fabric, a textile, or other thin flexible material.

In some embodiments, the latch portion may be configured to engage the buckle member 24, such that movement of the post member distally relative to the buckle member 24 is prevented. In some embodiments, at least a portion of the post member is flexible. In some embodiments, the latch portion may be movable and/or deflectable relative to the body portion. In some embodiments, the cantilevered leg may be movable toward and away from the body portion at and/or using the hinge portion.

In some embodiments, the body portion may be unitary with and/or integrally formed with the latch portion, the hinge portion, and/or the cantilevered leg as and/or from a single piece of material. In some embodiments, the post member may be formed from a single piece of wire, flat stock, or other suitable material as discussed herein. In some embodiments, the post member may be formed by further processing the single piece of wire, flat stock, or other suitable material, such as by machining, stamping, laser cutting, etc. Some suitable but non-limiting materials for the body portion, the latch portion, the hinge portion, and/or the cantilevered leg, for example metallic materials or polymeric materials, may be described below.

In some embodiments, an example actuator member may include a proximal end and a distal end. In use, the proximal end may be connected to and/or manipulated or otherwise actuated by a user, for example using the handle, to shift the medical implant 14 from a "delivery" configuration to a "deployed" configuration, and later to a "released" configuration. In some embodiments, the actuator member may be axially translatable relative to the buckle member 24. In some embodiments, the actuator member may be axially translatable within and/or through the channel of the buckle member 24.

In some embodiments, the actuator member and/or the elongated rod may be generally round, oblong, ovoid, rectangular, polygonal (i.e., two-sided, three-sided, four-sided, five-sided, six-sided, etc.) in shape. Other shapes, both regular and irregular, are also contemplated. In some embodiments, the actuator member may be formed from a single piece of wire, round stock, or other suitable material, as discussed herein. In some embodiments, the actuator member may be formed by further processing the single piece of wire, round stock, or other suitable material, such as by machining, stamping, laser cutting, etc. Some suitable but non-limiting materials for the actuator member, the elongated rod, and/or the distal end portion, for example metallic materials or polymeric materials, may be described below.

The materials that can be used for the various components of the medical implant system 10 (and/or other systems disclosed herein) and the various elements thereof disclosed herein may include those commonly associated with medical devices. For simplicity purposes, the following discussion makes reference to the delivery system 12 and/or the medical implant 14. However, this is not intended to limit the devices and methods described herein, as the discussion may be applied to other elements, members, components, or devices disclosed herein, such as, but not limited to, the braided anchor member 20, the actuator member, the locking mechanism, the post member, the buckle member 24, and/or elements or components thereof.

In some embodiments, the delivery system 12 and/or the medical implant 14, and/or components thereof (such as, but not limited to, the braided anchor member 20, the locking mechanisms, the actuator members, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system 12 and/or the medical implant 14, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery system 12 and/or the medical implant 14. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery system 12 and/or the medical implant 14 to achieve the same result.

In some embodiments, a degree of Magnetic Resonance Imaging (MRI) compatibility is imparted into the medical implant 14. For example, the delivery system 12 and/or the medical implant 14, and/or components or portions thereof, may be made of a material that does not substantially distort the image and create substantial artifacts (i.e., gaps in the image). Certain ferromagnetic materials, for example, may not be suitable because they may create artifacts in an MRI image. The delivery system 12 and/or the medical implant 14, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, a sheath or covering (not shown) may be disposed over portions or all of the delivery system 12 and/or the medical implant 14. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A replacement heart valve implant, comprising:
    a braided anchor member configured to actuate between an elongated delivery configuration and an expanded deployed configuration, the braided anchor member formed from a plurality of filaments;
    a circumferential seal member disposed about a distal portion of the braided anchor member, the circumferential seal member including a reinforcing band disposed at a distal end thereof; and
    a plurality of valve leaflets connected to the braided anchor member;
    wherein the reinforcing band is secured to the braided anchor member adjacent a distal end of the braided anchor member by a plurality of lashings, wherein each lashing is attached to two individual filaments of the plurality of filaments.

2. The replacement heart valve implant of claim 1, wherein the two individual filaments are crossing each other where each lashing is attached thereto.

3. The replacement heart valve implant of claim 1, wherein the two individual filaments are immediately adjacent each other where each lashing is attached thereto.

4. The replacement heart valve implant of claim 1, wherein at least a portion of the braided anchor member extends distally of the plurality of lashings.

5. The replacement heart valve implant of claim 4, wherein at least a portion of the braided anchor member extends distally of all of the plurality of lashings.

6. The replacement heart valve implant of claim 4, wherein at least a portion of each of the two individual filaments extends distally of each lashing attached thereto.

7. The replacement heart valve implant of claim 1, wherein each lashing comprises more than one suture member.

8. The replacement heart valve implant of claim 1, wherein the reinforcing band includes a fabric strip.

9. The replacement heart valve implant of claim 1, wherein each of the plurality of valve leaflets is secured directly to the reinforcing band.

10. A replacement heart valve implant, comprising:
    a braided anchor member configured to actuate between an elongated delivery configuration and an expanded deployed configuration, the braided anchor member formed from a plurality of filaments defining a body section, a proximal crown section, and a distal crown section;
    a circumferential seal member disposed about a distal portion of the braided anchor member, the circumferential seal member including a reinforcing band disposed at a distal end thereof; and
    a plurality of valve leaflets connected to the braided anchor member;
    wherein the proximal crown section includes a first plurality of end loops and a second plurality of end loops;
    wherein a proximalmost extent of the first plurality of end loops and the second plurality of end loops varies around a circumference of the braided anchor member.

11. The replacement heart valve implant of claim 10, wherein when the braided anchor member is in the deployed configuration the first plurality of end loops extends proximally to a first proximal extent and the second plurality of end loops extends proximally to a second proximal extent distal of the first proximal extent.

12. The replacement heart valve implant of claim 10, wherein the braided anchor member includes a plurality of buckle members fixedly attached thereto, the plurality of buckle members being configured to lock the braided anchor member in the deployed configuration.

13. The replacement heart valve implant of claim 12, wherein each of the plurality of buckle members is positioned circumferentially between adjacent end loops from the first plurality of end loops.

14. The replacement heart valve implant of claim 12, wherein each of the plurality of buckle members is positioned circumferentially over one of the second plurality of end loops.

15. The replacement heart valve implant of claim 12, wherein two of the first plurality of end loops and two of the second plurality of end loops is disposed circumferentially between adjacent buckle members.

16. The replacement heart valve implant of claim 10, wherein when the braided anchor member is in the elongated delivery configuration the first plurality of end loops extends farther proximally than the second plurality of end loops.

17. The replacement heart valve implant of claim 10, wherein the distal crown section includes a third plurality of end loops and a fourth plurality of end loops;
   wherein a distalmost extent of the third plurality of end loops and the fourth plurality of end loops varies around a circumference of the braided anchor member.

18. The replacement heart valve implant of claim 17, wherein when the braided anchor member is in the deployed configuration the third plurality of end loops extends distally to a first distal extent and the fourth plurality of end loops extends distally to a second distal extent proximal of the first distal extent.

19. The replacement heart valve implant of claim 17, wherein when the braided anchor member is in the elongated delivery configuration the third plurality of end loops extends farther distally than the fourth plurality of end loops.

20. The replacement heart valve implant of claim 10, wherein the braided anchor member is formed from a metallic material.

* * * * *